United States Patent
Bogdanov

(10) Patent No.: US 6,495,363 B2
(45) Date of Patent: Dec. 17, 2002

(54) IN-LINE COMPLETE SPECTRAL FLUORESCENT IMAGING OF NUCLEIC ACID MOLECULES

(75) Inventor: Valery Bogdanov, Baltimore, MD (US)

(73) Assignee: Orchid BioSciences, Inc., Princeton, NJ (US)

( * ) Notice: Subject to any disclaimer, the term of this patent is extended or adjusted under 35 U.S.C. 154(b) by 0 days.

(21) Appl. No.: 09/861,137

(22) Filed: May 18, 2001

(65) Prior Publication Data

US 2002/0009744 A1 Jan. 24, 2002

Related U.S. Application Data

(63) Continuation of application No. 09/135,569, filed on Aug. 18, 1998, now Pat. No. 6,245,507.

(51) Int. Cl.[7] ............................. C12Q 1/68; C12P 19/34; C12M 1/34; C07H 21/02; C07H 19/00
(52) U.S. Cl. ......................... 435/287.2; 435/6; 435/7.1; 435/91.2; 536/22.1; 536/23.1; 536/24.3; 536/24.31; 536/24.32; 536/24.33
(58) Field of Search .......................... 435/6, 7.1, 91.2, 435/287.2; 536/22.1, 23.1, 24.3, 24.31, 24.32, 24.33; 250/334; 204/461

(56) References Cited

U.S. PATENT DOCUMENTS

| | | | |
|---|---|---|---|
| 4,325,636 A | 4/1982 | Schiffner et al. | |
| 4,656,127 A | 4/1987 | Mundy | |
| 5,162,654 A | 11/1992 | Kostichka et al. | |
| 5,274,240 A | 12/1993 | Mathies et al. | |
| 5,470,710 A | 11/1995 | Weiss et al. | |
| 5,547,839 A | 8/1996 | Dower et al. | |
| 5,578,832 A | 11/1996 | Trulson et al. | |
| 5,667,656 A | 9/1997 | Kambara | |
| 5,674,743 A | 10/1997 | Ulmer | |
| 5,679,524 A | 10/1997 | Nikiforov et al. | |
| 5,817,462 A | 10/1998 | Garini et al. | |
| 5,871,628 A | 2/1999 | Dabiri et al. | |
| 6,008,492 A | * 12/1999 | Slater et al. | ................. 250/334 |
| 6,245,507 B1 | 6/2001 | Bogdanov | |

FOREIGN PATENT DOCUMENTS

| | | |
|---|---|---|
| WO | WO 95/00669 | 1/1995 |
| WO | WO 95/11995 | 5/1995 |
| WO | WO 95/17576 | 6/1995 |
| WO | WO 98/08085 | 2/1998 |

OTHER PUBLICATIONS

Bogdanov et al., "Multicolor instrumentation for direct fluorescent detection of nucleic acids microchip", Proc. SPIE 3259:156–164 (Apr. 1998).
Bogfanov et al., "Fluorescent imaging and quantitation of solid support bound nucleic acids", SPIE Proceeding, 2985:129–137 (1997).
Fodor et al., "Multiplexed biochemical assays with biological chips," Nature, 364:555–556 (1993).
Ginot, "Oligonucleotide Micro–Arrays for Identification of Unknown Mutations: How Far from Reality?," Human Mutation, 10(1):1–10 (1997).
Guo et al., "Direct fluorescence analysis of genetic polymorphisms by hybridization with oligonucleotide arrays on glass supports," Nucleic Acids Research, 22(24):5456–5465 (1994).
Hacia et al., "Detection of heterozygous mutations in breal using high density oligonucleotide arrays and two–colour fluorescence analysis," Nature Genetics, 14:441–447 (1996).
Head et al., "Nested genetic bit analysis (N–GBA) for mutation detection in the p53 tumor suppressor gene," Nucleic Acids Res. 25:5065–5071 (1997).
Ives et al., "Fluorescence Detection Applied to Non–Electrophoretic DNA Diagnostics on Oligonucleotide Arrays," SPIE Proceeding 2680:258–269 (1996).
Jalanko et al., "Screening for Defined Cystic Fibrosis Mutations By Solid–Phase Minisequencing," Clin. Chem. 38:39–43 (1992).
Karger et al., "Multiwavelength fluorescence detection for DNA sequencing using capillary electrophoresis," Nucleic Acids Res. 19:4955–4962 (1991).
Kheterpal et al., "DNA sequencing using a four–colour confocal fluorescence capillary array scanner," Electrophoresis 17:1852–1859 (1996).
Kostichka et al., "High Speed Automated DNA Sequencing in Ultrathin Slab Gels," Bio/Technology 10:78–81 (1992).
Li and Yeung, "Simple Two–Color Base–Calling Schemes for DNA Sequencing Based on Standard Four–Label Sanger Chemistry," Applied Spectroscopy, 49(10):1528–1522 (1995).
McGall et al., "Light–directed synthesis of high–density oligonucleotide arrays using semiconductor photoresists," Proc. Natl. Acad. Sci (USA), 93:13555–13560 (1966).
Nikiforov et al., "Genetic Bit Analysis: a solid phase method for typing single nucleotide polymorphisms," Nucleic Acids Research, 22:4167–4175 (1994).
Nikiforov et al., "The Use of Phosphorothioate Primers and Exonuclease Hydrolysis for the Preparation of Single–Stranded PCR Products and their Detection by Solid–Phase Hybridization," PCR Methods and Applications, 3:285–291 (1994).
Pastinen et al., "Multiplex, fluorescent, solid–phase minisequencing for efficient screening of DNA sequence variation," Clin. Chem. 42:13191–1397 (1996).

(List continued on next page.)

*Primary Examiner*—Jeffrey Shaw
(74) *Attorney, Agent, or Firm*—Kalow & Springut LLP

(57) ABSTRACT

The present invention provides a hyperspectral imaging apparatus and methods for employing such an apparatus for multi-dye/base detection of a nucleic acid molecule coupled to a solid surface.

10 Claims, 7 Drawing Sheets

OTHER PUBLICATIONS

Pastinen et al., "Minisequencing: A Specific Tool for DNA Analysis and Diagnostics on Oligonucleotide Arrays," Genome Res. 7:606–614 (1997).

Pease et al., "Light–generated oligonucleotide arrays for rapid DNA sequence analysis," Proc. Natl. Acad. Sci. (USA), 91(11):5022–5026 (1994).

Prober et al., "A System for Rapid DNA Sequencing with Fluorescent Chain–Terminating Dideoxynucleotides," Science, 238:336–341 (1987).

Sandison and Webb, "Background rejection and signal–to–noise optimization in confocal and alternative fluorescence microscopes," Applied Optics, 33: 603–615 (1994).

Sapolsky and Lipshutz, "Mapping Genomic Library Clones Using Oligonucleotide Arrays," Genomics, 33:445–456 (1996).

Schena et al., "Parallel human genome analysis: Microarray–based expression monitoring of 1000 genes," Proc. Natl. Acad. Sci. (USA) 93:10614–10619 (1996).

Shumaker et al., "Mutation Detection by Solid Phase Primer Extension," Hum. Mutation 7:346–354 (1996).

Smith et al., "Fluorescence detection in automated DNA sequence analysis," Nature 321:674–679 (1986).

Taylor et al., "Automated analysis of multiplex microsatellites," J. Med. Genet. 31:937–94 (1994).

Yager et al., "High–speed DNA sequencing in ultrathin slab gels," Curr Opinion Biotechnol. 8:107–113 (1997).

* cited by examiner

IN-LINE COMPLETE SPECTRAL FLUORESCENT IMAGING OF NUCLEIC ACID MOLECULES

CROSS-REFERENCE TO RELATED APPLICATION

This application is a continuation of U.S. patent application Ser. No. 09/135,569, filed Aug. 18, 1998 and now U.S. Pat. No. 6,245,507, which application is herein incorporated by reference.

FIELD OF THE INVENTION

The present invention is in the field of nucleic acid sequencing, and particularly relates to the use of the fluorescent reagents in the sequencing of nucleic acid molecules. More specifically, the present invention is in the field of sequencing via fluorescent nucleic acid molecules immobilized to a microchip and apparatuses for the same.

BACKGROUND OF THE INVENTION

The most commonly used methods of nucleic acid sequencing are the dideoxy-mediated chain termination method, also known as the "Sanger Method" (Sanger et al., J. Molec. Biol. 94:441 (1975); see also Prober et al., Science 238:336–340 (1987), both herein incorporated by reference in their entirety) and the "chemical degradation method," also known as the "Maxam-Gilbert method" (Maxam et al., Proc. Natl. Acad. Sci. (U.S.A.) 74:560 (1977), herein incorporated by reference in its entirety). Such methods are disclosed in Maniatis et al., Molecular Cloning, a Laboratory Manual, 2nd Edition, Cold Spring Harbor Press, Cold Spring Harbor, N.Y. (1989); Zyskind et al., Recombinant DNA Laboratory Manual, Academic Press, Inc., New York (1988), both herein incorporated by reference in their entirety.

Both the dideoxy-mediated method and the Maxam-Gilbert method of DNA sequencing require the prior isolation of the DNA molecule that is to be sequenced. The sequence information is obtained by subjecting the reaction products to electrophoretic analysis (typically using polyacrylamide gels). Thus, a sample is applied to a lane of a gel, and the various species of nested fragments are separated from one another by their migration velocity through the gel.

In response to the difficulties encountered in employing gel electrophoresis to analyze sequences, several alternative methods have been developed. In one such method, a solid phase array of nucleic acid molecules is employed. The array consists of combinatorial (i.e., random or pseudo-random) nucleic acid molecules. Chetverin et al. provides a general review of solid-phase oligonucleotide synthesis and hybridization techniques (Chetverin et al., Bio/Technology 12:1093–1099 (1994), herein incorporated by reference in its entirety).

Macevicz, for example, describes a method for determining nucleic acid sequence via hybridization with multiple mixtures of oligonucleotide probes. In accordance with this method, the sequence of a target polynucleotide is determined by permitting the target to sequentially hybridize with sets of probes having an invariant nucleotide at one position, and a variant nucleotides at other positions (U.S. Pat. No. 5,002,867, herein incorporated by reference in its entirety). The Macevicz method determines the nucleotide sequence of the target by hybridizing the target with a set of probes, and then determining the number of sites that at least one member of the set is capable of hybridizing to the target (i.e., the number of "matches"). This procedure is repeated until each member of sets of probes has been tested.

Beattie et al. have described a protocol for the preparation of terminal amine-derivatized 9-mer oligonucleotide arrays on ordinary microscope slides (Beattie et al., Molec. Biotech. 4:213–225 (1995), herein incorporated by reference in its entirety). These oligonucleotide arrays can hybridize DNA target strands of up to several hundred bases in length and can discriminate against mismatches.

Drmanac has described a method for sequencing nucleic acid by hybridization using nucleic acid segments on different sectors of a substrate and probes which discriminate between a one base mismatch (Drmanac EP 797683, herein incorporated by reference in its entirety). Gruber describes a method for screening a sample for the presence of an unknown sequence using hybridization sequencing (Gruber, EP 787183, herein incorporated by reference in its entirety).

In contrast to the "Sanger Method" and the "Maxam-Gilbert method," which identify the entire sequence of nucleotides of a target polynucleotide, "microsequencing" methods determine the identity of only a single nucleotide at a "predetermined" site. Such methods have particular utility in determining the presence and identity of polymorphisms in a target polynucleotide.

Because single nucleotide polymorphisms constitute sites of variation flanked by regions of invariant sequence, their analysis requires no more than the determination of the identity of the single nucleotide present at the site of variation; it is unnecessary to determine a complete gene sequence for each patient. Several methods have been developed to facilitate the analysis of such single nucleotide polymorphisms.

The GBA™ Genetic Bit Analysis method disclosed by Goelet et al. (WO 92/15712, herein incorporated by reference in its entirety) is a particularly useful microsequencing method. In GBA™, the nucleotide sequence information surrounding a predetermined site of interrogation is used to design an oligonucleotide primer that is complementary to the region immediately adjacent to, but not including, the predetermined site. The target DNA template is selected from the biological sample and hybridized to the interrogating primer. This primer is extended by a single labeled dideoxynucleotide using DNA polymerase in the presence of at least two, and most preferably all four chain terminating nucleoside triphosphate precursors.

Mundy (U.S. Pat. No. 4,656,127, herein incorporated by reference in its entirety) discusses alternative microsequencing methods for determining the identity of the nucleotide present at a particular polymorphic site. Mundy's method employs a specialized exonuclease-resistant nucleotide derivative. A primer complementary to the allelic sequence immediately 3'-to the polymorphic site is permitted to hybridize to a target molecule obtained from a particular animal or human. If the polymorphic site on the target molecule contains a nucleotide that is complementary to the particular exonucleotide-resistant nucleotide derivative present, then that derivative will be incorporated by a polymerase onto the end of the hybridized primer. Such incorporation renders the primer resistant to exonuclease, and thereby permits its detection. Since the identity of the exonucleotide-resistant derivative of the sample is known, a finding that the primer has become resistant to exonucleases reveals that the nucleotide present in the polymorphic site of the target molecule was complementary to that of the nucleotide derivative used in the reaction. Mundy's method has the advantage that it does not require the determination of large amounts of extraneous sequence data. It has the disadvantages of destroying the amplified target sequences, and unmodified primer and of being extremely sensitive to the rate of polymerase incorporation of the specific exonuclease-resistant nucleotide being used.

Cohen et al. (French Patent 2,650,840; PCT Appln. No. WO91/02087, both of which are herein incorporated by reference in their entirety) discuss a solution-based method for determining the identity of the nucleotide of a polymorphic site. As in the Mundy method of U.S. Pat. No. 4,656,127, a primer is employed that is complementary to allelic sequences immediately 3'-to a polymorphic site. The method determines the identity of the nucleotide of that site using labeled dideoxynucleotide derivatives, which, if complementary to the nucleotide of the polymorphic site will become incorporated onto the terminus of the primer.

In contrast to the method of Cohen et al. (French Patent 2,650,840; PCT Appln. No. WO91/02087), the GBA™ method of Goelet et al. can be conducted as a heterogeneous phase assay, in which the primer or the target molecule is immobilized to a solid phase. It is thus easier to perform, and more accurate than the method discussed by Cohen. The method of Cohen has the significant disadvantage of being a solution-based extension method that uses labeled dideoxynucleoside triphosphates. In the Cohen method, the target DNA template is usually prepared by a DNA amplification reaction, such as PCR, that uses a high concentration of deoxynucleoside triphosphates, the natural substrates of DNA polymerases. These monomers will compete in the subsequent extension reaction with the dideoxynucleoside triphosphates. Therefore, following the PCR reaction, an additional purification step is required to separate the DNA template from the unincorporated dNTPs. Because it is a solution-based method, the unincorporated dNTPs are difficult to remove and the method is not suited for high volume testing.

Cheesman (U.S. Pat. No. 5,302,509, herein incorporated by reference in its entirety) describes a method for sequencing a single stranded DNA molecule using fluorescently labeled 3'-blocked nucleotide triphosphates. An apparatus for the separation, concentration and detection of a DNA molecule in a liquid sample has been described by Ritterband et al. (PCT Patent Application No. WO95/17676, herein incorporated by reference in its entirety). Dower et al. U.S. Pat. No. 5,547,839, herein incorporated by reference in its entirety) describes a filter based detection system for the simultaneous parallel sequencing of an immobilized primer using fluorescent labels.

The delayed extraction PinPoint MALDI-TOF mass spectrometry method is a method for determining the identity of the incorporated non-extendible nucleotide by measuring the change in mass of the extended primer (Haff et al., *Genome Methods* 7:378–388 (1997), the entirety of which is herein incorporated by reference).

Chee et al. (WO95/11995, herein incorporated by reference in its entirety) describes an array of primers immobilized onto a solid surface. Chee et al further describes a method for determining the presence of a mutation in a target sequence by comparing against a reference sequence with a known sequence.

Several primer-guided nucleotide incorporation procedures for assaying polymorphic sites in DNA have been described (Komher et al., *Nucl. Acids. Res.* 17:7779–7784 (1989); Sokolov, *Nucl. Acids Res.* 18:3671 (1990); Syvänen et al., *Genomics* 8:684–692 (1990); Kuppuswamy et al., *Proc. Natl. Acad. Sci.* (*U.S.A.*) 88:1143–1147 (1991); Prezant et al., *Hum. Mutat.* 1:159–164 (1992); Ugozzoli et al., *GATA* 9:107–112 (1992); Nyrén et al., *Anal. Biochem.* 208:171–175 (1993); and Wallace, WO89/10414, all of which are herein incorporated by reference in their entirety). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvänen et al., *Amer. J. Hum. Genet.* 52:46–59 (1993), herein incorporated by reference in its entirety). Such a range of locus-specific signals could be more complex to interpret, especially for heterozygotes, compared to the simple, ternary (2:0, 1:1, or 0:2) class of signals produced by the GBA™ method. In addition, for some loci, incorporation of an incorrect deoxynucleotide can occur even in the presence of the correct dideoxynucleotide (Komher et al., *Nucl. Acids. Res.* 17:7779–7784 (1989)). Such deoxynucleotide misincorporation events may be due to the Km of the DNA polymerase for the mispaired deoxy-substrate being comparable, in some sequence contexts, to the relatively poor Km of even a correctly base paired dideoxy-substrate (Kornberg, A. et al., In: *DNA Replication, Second Edition* (1992), W. H. Freeman and Company, New York; Tabor, S. et al., *Proc. Natl. Acad. Sci.* (U.S.A) 86:4076–4080 (1989), both of which are herein incorporated by reference in their entirety). This effect would contribute to the background noise in the polymorphic site interrogation.

An alternative microsequencing approach, the "Oligonucleotide Ligation Assay" ("OLA") (Landegren et al., *Science* 241:1077–1080 (1988), herein incorporated by reference in its entirety) has also been described as being capable of detecting single nucleotide polymorphisms. The OLA protocol uses two oligonucleotides which are designed to be capable of hybridizing to abutting sequences of a single strand of a target. One of the oligonucleotides is biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson et al. have described a nucleic acid detection assay that combines attributes of PCR and OLA (Nickerson et al., *Proc. Natl. Acad. Sci.* (*U.S.A.*) 87:8923–8927 (1990), herein incorporated by reference in its entirety). In this method, PCR is used to achieve the exponential amplification of target DNA, which is then detected using OLA. In addition to requiring multiple, and separate processing steps, one problem associated with such combinations is that they inherit all of the problems associated with PCR and OLA.

Boyce-Jacino et al. have described a method for sequencing a polynucleotide using nested GBA (U.S. patent application Ser. No. 08/616,906, herein incorporated by reference in its entirety). In that method, an array of nested primer oligonucleotides is immobilized to a solid support. A target nucleic molecule is hybridized to the array of nested primer oligonucleotides and the hybridized array is sequenced using GBA.

Pastinen et al. describe a method for the multiplex detection of mutations wherein the mutations are detected by extending immobilized primers, that anneal to the template sequences immediately adjacent to the mutant nucleotide positions, with a single labeled dideoxynucleotide using a DNA polymerase (Pastinen et al., *Genome Res.* 7:606–614

(1997), herein incorporated by reference in its entirety). In this method, the oligonucleotide arrays were prepared by coupling one primer per mutation to be detected on a small glass area. Pastinen et al. have also described a method to detect multiple single nucleotide polymorphisms in an undivided sample (Pastinen et al, Clin. Chem. 42:13191–1397 (1996), herein incorporated by reference in its entirety). According to this method, the amplified DNA templates are first captured onto a manifold and then, with multiple minisequencing primers, single nucleotide extension reactions are carried out simultaneously with fluorescently labeled dideoxynucleotides.

Jalanko et al. applied the solid-phase minisequencing method to the detection of a mutation causing cystic fibrosis (Jalanko et al., Clin. Chem. 38:39–43 (1992), herein incorporated by reference in its entirety). In the method of Jalanko et al., an amplified DNA molecule which is biotinylated at the 5' terminus is bound to a solid phase and denatured. A detection primer, which hybridizes immediately before the mutation, is hybridized to the immobilized single stranded template and elongated with a single, labeled deoxynucleoside residue. Shumaker et al. describes another solid phase primer extension method for mutation detection (Shumaker et al., Hum. Mutation 7:346–354 (1996), herein incorporated by reference in its entirety). In this method, the template DNA was annealed to an oligonucleotide array, extended with $^{32}$P dNTPs and analyzed with a phosphoimager. The grid position of the oligonucleotide identified the mutation site and the extended base identified the mutation.

Caskey et al. describe a method of analyzing a polynucleotide of interest using one or more sets of consecutive oligonucleotide primers differing within each set by one base at the growing end thereof (Caskey et al., WO 95/00669, herein incorporated by reference in its entirety). The oligonucleotide primers are extended with a chain terminating nucleotide and the identity of each terminating nucleotide is determined.

In conventional fluorescent-based sequencing applications, the predominate method of base calling involves the use of four dye label terminators that have different emission spectra (as used herein, base calling refers to identifying the identity of the nucleotide base). One such application employs laser excitation and a cooled CCD (charged coupled device) detector (Kostichka and Smith, U.S. Pat. No. 5,162,654, herein incorporated by reference in its entirety) for the parallel detection of four fluorescently labeled DNA sequencing reactions during their electrophoretic separation in ultrathin (50–100 microns) denaturing polyacrylamide gels (Kostichka et al., Bio/Technology 10:78–81 (1992), herein incorporated by reference in its entirety).

Weiss et al. describes another fluorescent-based sequencing application (U.S. Pat. No. 5,470,710, herein incorporated by reference in its entirety). That method is an enzyme linked fluorescence method for the detection of nucleic acid molecules.

In these applications, spectral recognition of different dyes is primarily accomplished by capturing fluorescence emissions in specific spectral regions using one or more excitation wavelengths. One problem with this approach is the "cross-talk" of different dyes due to the relatively large width of dye spectra. Spectral cross-talk is one source of false recognition of dyes, resulting in base miscalling in fluorescent-based DNA sequence analysis (as used herein, the term miscalling refers to an error in identifying the identity of the nucleotide base). The miscalling rate depends primarily on the signal-to-noise ratio (SNR) and the detection system's spectral selectivity. Basically, the miscalling rate increases when the SNR decreases. Therefore, if the spectrally recognized emission is weak, the spectral selectivity of the instrument will have to be improved to lower the miscalling rate.

It has been reported that the spectral cross-talk in macroscale, gel-based DNA fluorescent sequencing has been resolved by improved dye-terminator biochemistry, optimization of filter transmission spectra and software manipulation using an instrument of relatively low spectral selectivity (Yager et al., Curr. Opinion Biotechnol. 8:107–113 (1997), herein incorporated by reference in its entirety). For example, the ABI gel sequencer (ABI, Applied Biosystems, Inc., Foster City, Calif.) has the capability of generating an acceptable base calling error rate of 2% (ABI Prism) using a single excitation wavelength and filter-based detection optics. In the case of microarray fluorescent detection, the spectral cross-talk problem is more difficult to overcome due to the significantly smaller size of the reaction spots, which require high spatial resolution power and generate very limited numbers of detectable fluorescence photons. This miniaturization/detection problem is well-known in the field of DNA sequencing by microcapillary electrophoresis. Several methods, including the use of two excitation wavelengths (Li and Yeung, Applied Spectroscopy 49:1528–1533 (1995), herein incorporated by reference in its entirety) and multi-wavelength (complete spectrum) fluorescence detection (Karger et al., NucleicAcids Res. 19:4955–4962 (1991), herein incorporated by reference in its entirety) have been developed to improve the spectral selectivity and identification in microcapillary multi-color sequencing.

Specific dye/base recognition on the microchip platform, which is considered to be a two-dimensional platform, is reported to be more complicated than in microcapillary methods, which are considered to be a one-dimensional platform. The two-dimensional nature of the microarray provides advantages in processing through-put due to the parallelism. However, it also requires a detection method that is compatible with its two-dimensional platform, in order for the through-put potential to be realized. There have been at least two microarray fluorescent detectors, including the "genescanner" from Hewlett Packard (Santa Clara, Calif.)(Taylor et al., J. Med. Genet. 31: 937–94 (1994), herein incorporated by reference in its entirety) and a confocal scanner (General Scanning, Inc., Boston), developed using filter-based confocal optics configuration, a one-dimensional (1-D) detector (the photomultiplier tube, PMT) and narrow bandpass interference filters to obtain sensitive detection and spectral identification of array emissions. The confocal configuration is used in these fluorescent detection instruments to obtain high spatial resolution and to reduce background emission by confining the detection volume (Sandison and Webb, Applied Optics 33:603–615 (1994), herein incorporated by reference in its entirety).

The disadvantages of confocal microarray scanners include: 1) low through-put caused by the necessity of sequential, point-by-point scanning of the microarray, 2) use of moving optical-mechanical parts for scanning, 3) use of expensive qualitative focusing/collection optics, 4) high power excitation requirement due to the significant loss of collected emissions in the confocal pinhole, and 5) repeated scanning required for multi-color detection. Therefore, although confocal filter-based microchip scanners can be potentially used for spectral recognition of array emissions, they are inherently expensive and low through-put. In addition, for multi-color detection, photobleaching of the dyes under powerful laser excitation during repeated scans may further complicate the spectral analysis.

Four-color confocal fluorescence capillary array scanner sequencing apparatuses have been described (Mathies et al., U.S. Pat. No. 5,274,240; Kheterpal et al., *Electrophoresis* 17:1852–1859 (1996), both of which are herein incorporated by reference in their entirety). Kheterpal's array scanner utilizes a single laser wavelength of 488 nm to collect data from up to 25 capillaries in parallel. A capillary electrophoresis apparatus for the detection of nucleic acid sequences which employs a He-Ne laser has been described (Kambara, U.S. Pat. No. 5,667,656, herein incorporated by reference in its entirety). Ulmer describes another capillary sequencing apparatus employing fluorescently labeled bases and a laser detector (Ulmer, U.S. Pat. No. 5,674,743, herein incorporated by reference in its entirety).

Ives et al. describe a method for the detection of fluor-labeled (fluorescein, eosin, tetramethyl-rhodamine, Lissamine and Texas Red) dideoxynucleotides using a commercially available plate reader (Cytofluor II) (Ives et al., SPIE Proceeding 2680:258–269 (1996), herein incorporated by reference in its entirety). Ives et al. also disclose an experimental optical setup to detect fluorescence from fluor-labeled GBA™ dideoxynucleotides which uses excitation light from an air cooled argon laser at 488 nm with collection optics consisting of a spherical collection lens, Schott filters, fiber optic collection (collectively a filter-based optics configuration), an imaging spectrometer and a 0° C. thermoelectrically-cooled CCD camera. In addition, the optical system is used to detect the fluorescence emitting from a single reaction spot on a microchip.

Bogdanov et al. disclose the fluorescent imaging and quantification of solid support-bound nucleic acids (Bogdanov et al., SPIE Proceeding 2985:129–137 (1997), herein incorporated by reference in its entirety). The Bogdanov et al. reference discloses direct multicolor fluorescent imaging of a GBA™ array (GBA™ microchip) on a solid-state support with low background emission (glass microscope slide) for simultaneous (CCD camera) and sequential (commercial FluorImagers) reaction spots reading at excitation of various lasers. Bogdanov et al. employ a filter-based confocal optics configuration. Two-color fluorescent images of oligonucleotides labeled by fluorescein and CY3 were reported, as was CCD-based imaging of a direct multispot GBA™ image extension detection reaction using fluorescein-labeled ddATP.

Multi-color fluorescent detection has been used in macroscale gel-based sequencing. The present invention provides a microscale sequencing technique and apparatus with significant advantages over other solid-phase sequencing techniques and apparatuses. These advantages include simplification of sample and reagent processing, rapid and sensitive detection, as well as compatibility with high through-put processing. Through strategic combinations of a highly sensitive CCD detector with parallel image spectrometry, hyperspectral imaging detection on SPS microarrays has provided for a low-cost sequence analysis technology.

SUMMARY OF THE INVENTION

The present invention provides a hyperspectral fluorescent imaging apparatus for microarray detection which comprises: (a) a light source, wherein the light source is capable of emitting a transmission beam; (b) an expansion lens; (c) a focusing lens, wherein the focusing lens focuses said transmission beam into a thin focus line; (d) a collection lens; (e) an imaging spectrometer; and (f) a detector.

The hyperspectral fluorescent imaging apparatus of the present invention may further comprise a translation stage.

The present invention further provides a method for hyperspectral imaging a fluorescently labeled nucleotide analog, wherein said method comprises the steps: (a) emitting a transmission beam from a light source; (b) expanding the transmission beam by passing said transmission beam through an expansion lens; (c) focusing the expanded transmission beam into a focus line by passing the expanded transmission beam through a focusing lens; (d) contacting the fluorescently labeled nucleotide analog with the focused transmission beam, wherein the contact between the focused transmission line and the fluorescently labeled nucleotide analog excites said fluorescently labeled nucleotide analog to emit a fluorescent emission; (e) collecting the fluorescent emission with a collection lens; (f) projecting the collected fluorescent emission into an imaging spectrometer; (g) detecting the projected fluorescent emission using a detector.

DETAILED DESCRIPTION OF THE PREFERRED EMBODIMENTS

Advancements in the research and diagnostic applications of oligonucleotide arrays, such as differential display, sequencing by hybridization and primer extension genotyping, have facilitated the development of low-cost, sensitive and rapid array analysis methods. However, the processing power of the solid-phase sequencing strategy can only be fully realized through the incorporation of multi-color, direct fluorescent detection methodology. Single color primer extension, like single color Sanger sequencing, requires four separate reactions (G, A, T, C) to determine which combination of up to two bases (at heterozygous sites) are present in the target. Multi-color primer extension, like four-color fluorescent sequencing, enables a single reaction to be performed with separation at the data analysis stage. Microarray-based primer extension biochemistry has been used for rapid and sensitive mutation scanning with single color fluorescent detection (Head et al., *Nucleic Acids Res.* 25:5065–5071 (1997), herein incorporated by reference in its entirety).

The present invention provides both a hyperspectral fluorescent imaging apparatus and methods for employing such an apparatus for multi-dye/base detection on a microarray. More specifically, the present invention describes a multi-color, solid-phase, hyperspectral (complete spectrum) imaging apparatus and methods thereof which enables highly sensitive, rapid and low-cost analysis of primer extension arrays. The present invention further provides a rapid and cost-effective fluorescent detection apparatus and methods thereof with the capability of spectrally discriminating four dye labels on a high density DNA microarray. The method of the present invention has general applicability to the analysis of multi-color arrays in other tests, such as hybridization or differential display. Under one embodiment, the present invention can be used to detect a mutation in a gene that, for example, plays a causative role in diseases such as cancer (p53 and BRCA2 are two examples of such genes).

The present invention offers a significant advantage over traditional gel-based mutation detection methods in the areas of through-put, cost, reliability and operational simplicity. The present invention can accurately identify heterozygous mutations. Preferably, analysis of both strands is performed to reduce potential mis-calling. Under another preferred embodiment, genotyping of wild type DNA (as a reference strand) for comparison of background noise levels is performed to improve the ability to accurate identify "true" heterozygotes. The present invention can be used to detect the incorporation of labeled dye terminators either in solution, or on microarrays.

I. In-Line Hyperspectral Imaging Aparatus

A. Signaling and Detection Aparatus

Figure 1:
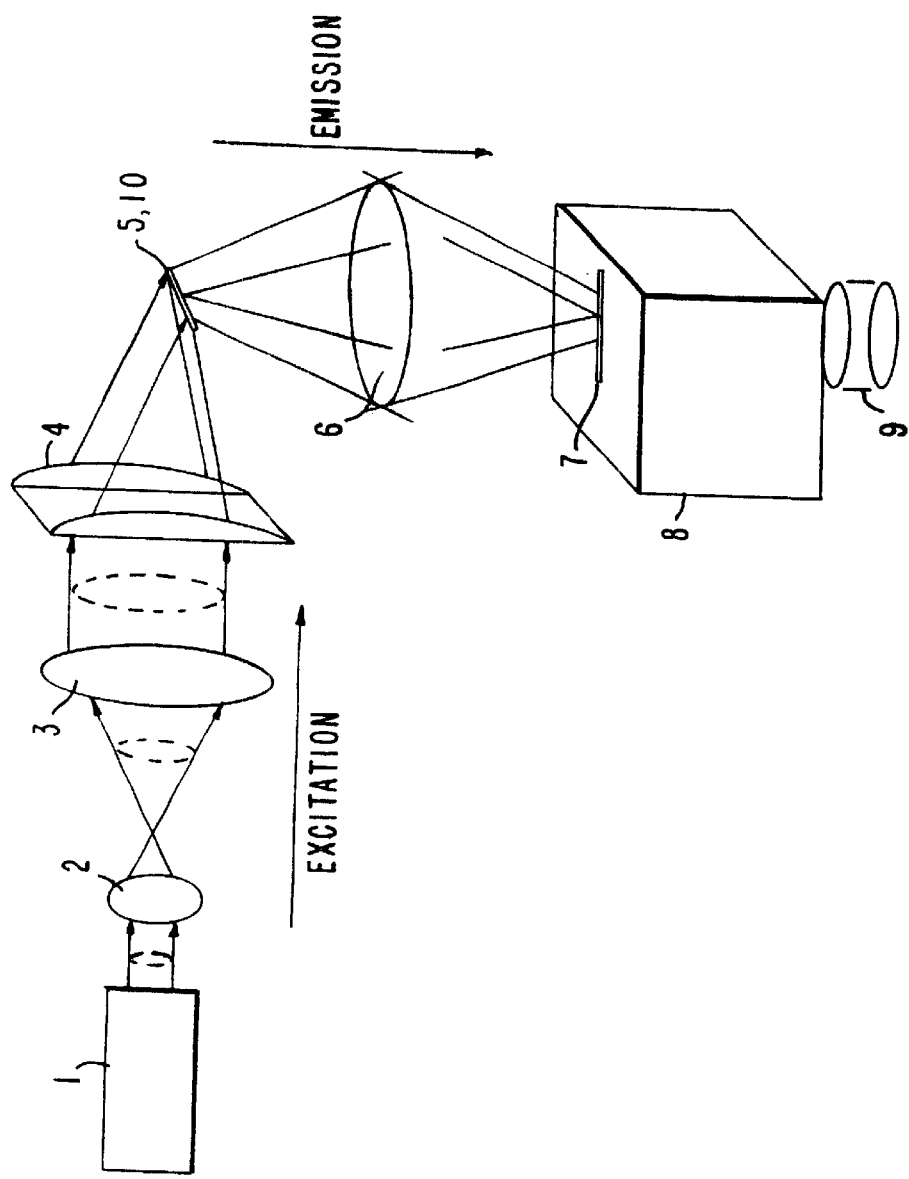
FIG. 1 provides a schematic illustration of the hyperspectral sequencing apparatus of the present invention.
Figure 2:
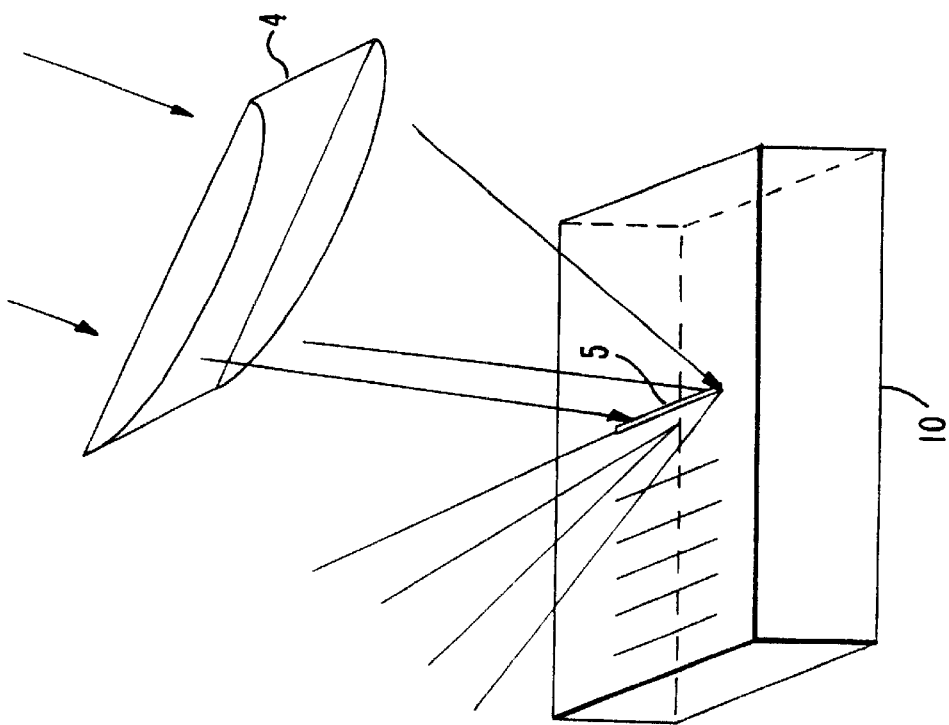
FIG. 2 provides an exploded illustration of the boxed region of FIG. 1.

The present invention provides a hyperspectral (complete spectrum) detection apparatus. The preferred embodiment of the present invention, which is illustrated in FIG. 1, comprises a light source (1), a set of expansion lenses (2 and 3), a focusing lens (4), a focus line (5), a nucleic acid microchip (10), a collection lens (6), an imaging spectrometer (8) having a slit (7), and a detector (9).

Preferably, the light source (1) of the present invention is capable emitting a hyperspectral (complete spectrum) emission beam. Preferably, the light source (1) of the present invention is a laser. More preferably, the light source (1) of the present invention is an Ar laser. The preferred Ar laser of the present invention is a CW Ar laser. A CW Ar laser suitable for use in the present invention is the air-cooled argon ion laser, model 532 from Omnichrome, Inc. Under alternative embodiments, other lasers, such as a He-Ne laser, a diode laser, a mode-locked Ti:saphire laser, etc., can be used in the present invention. The light source of the present invention is preferably designed with the flexibility and the capability of shifting the excitation/detection region. This feature allows for rapid shifting of the detection region into a lower background area (red/near IR region). Thus, red/NIR dye-labeled ddNTPs can be used in the present invention.

Preferably, the emission beam of the present invention passes through at least one expansion lens (2). More preferably, the emission beam of the present invention passes through at least two expansion lenses (2 and 3). The expansion lens acts to expand the emission beam from the light source. Preferably, the expansion lens of the present invention is a spherical expansion lens. Preferably, expansion lens (2) is a 20×microscope objective. Such lenses are commercially available from Nikon, Inc. Preferably, expansion lens (3) is a spherical lens with a focal length of 10 cm. Such lenses are commercially available from Newport Corp.

Preferably, the emission beam of the laser of the present invention is focused by a focusing lens (4). Preferably, focusing lens (4) is a cylindrical lens with a focal length of 10 cm. Such lenses are commercially available from Newport Corp. The focusing lens condenses the emission beam in a single axis. Thus, a focusing lens can be used to focus the emission beam into a thin focus line (5). By focusing the emission beam into a thin focus line, the present invention permits the excitation of multiple array sights along a single direction (e.g., array row) in parallel. Preferably, the focusing lens of the present invention is cylindrical. Under one embodiment, the focus line of the emission beam in the focus plane is approximately 1×0.02 cm. However, it is understood that the focus line of the emission beam in the focus beam can be modified by one of skill in the art. Preferably, the focus line of the laser beam in the focus plane is of approximately the same length as the solid support upon which the sequencing regents of the present invention are situated. Preferably, the width of the focus line of the laser beam in the focus plane is narrow enough such that the focused line of the laser beam in the focus plane can only excite one row of sequencing reagents at any given moment. Thus, the present invention provides an apparatus for the parallel hyperspectral detection emission of multiple array sites in a microchip (10).

A collection lens (6) can be used to project the fluorescent emission from the illuminated microchip (10) along the entrance slit (7) of an imaging spectrometer (8). Preferably, collection lens (6) is a bi-convex lens. More preferably, the bi-convex collection lens (6) has a focal length (F) of 100 mm and a f/# of 1.9. Such lenses are commercially available from Newport Corp. Preferably, the collection lens of the present invention is a spherical collection lens. A spectrometer suitable for use in the present invention is the model 250 1S Imaging Spectrometer (Cromex, Inc.)

The multiple spectra of reaction spots on the microchip array sites in the laser illuminated area can then be simultaneously detected on the focal plane of the imaging spectrometer by a detector (9) which is capable of parallel spectral fluorescence detection. A cooled CCD detector is the preferred detector of the present invention because of its ability to detect low intensity signals (see, for example, Sheppard, *Confocal Microscopy: Basic Principles and System Performance* In: *Multidimensional Microscopy*, P. C. Cheng et al. eds., Springer-Verlag, N.Y., pp. 1–51 (1994), herein incorporated by reference in its entirety). Preferably, the cooled CCD detector of the present invention has a detection area of approximately 1000×1000 pixels wherein the size of each pixel is around 9 microns. Preferably, the cooled CCD camera has a readout rate of greater than 100 KB/sec. and a signal to noise ratio of approximately 10:1 at an illumination rate of approximately 100 photons per pixel. Cooled CCD detectors with the above parameters are suitable for use in the hyperspectral parallel detection apparatus of the present invention.

Under a more preferred embodiment, the CCD camera of the present invention has a high detection quantum efficiency (probability of single photon detection up to 80%), a high spatial resolution (pixel size as small as 5 microns) and sensitivity in a wide range of spectral regions (visible to near IR region), which overlap the emission spectra of the most commonly used dye-labeled terminators. More preferably, the CCD camera of the present invention allows the simultaneous capture of a large volume of information (detection area up to 4000×4000 pixels) and rapid data transfer (up to 5 Mb per second). Therefore, the parallel capturing of an entire microarray spectral image can be accomplished in real-time. CCD cameras suitable for use in the present invention include the SPECIM-1A camera (First Magnitude Corp.).

Alternatively, a photomultiplier ("PMT") with related optics modification may be used in the present invention. However, a CCD detector remains the preferred embodiment over a PMT in microchip fluorescent detection because of the CCD's compatibility with the 2-D microchip's metrics. As used herein, the phrase 2-D microchip's metrics means that the microchip is a plane detection object. In other words, the metrics of the detected object (microarray) is 2 dimensional. Detection efficiency is maximized when the object and detector metrics are matched. With a CCD, it is not necessary to scan the microarray point-by-point, as in a PMT, and a CCD allows for parallel fluorescent imaging of the entire DNA chip.

Under a preferred embodiment, the microchip array can be translated across the excitation laser beam by use of a translation stage thereby allowing complete spectral detection of multiple spot microchip fluorescent images across the entire microchip array. The phrase "translation stage," as used herein, refers to a device that produces a linear movement of an object. Under a preferred embodiment, the present invention employs an automated, single-axis translation stage to move the array and illuminate the different rows of the array sites by the excitation light. A translation stage suitable for use in the present invention is the Acturator 850B, Motion controller PMC 100; (Newport Corp., Irvine, Calif.). However, dual-axis translation stage devices are also suitable for use in the present invention.

Under a preferred sub-embodiment, the hyperspectral detection apparatus of the present invention employs a grating element. A grating element is a dispersive element of a spectrometer. The size and specification of the grating element is defined by the spectrometer manufacturer. A spectrometer having a grating element suitable for use in the present invention is the Imaging spectrometer 250IS (Chromex, Inc., Albuquerque, N. Mex.). The Imaging spectrometer 250IS grating element uses a ruled grating with 150 groove/mm.

Preferably, the parallel imaging spectrometry apparatus of the present invention combines spatial and spectral resolution to maximize the analytical power of optical instrumentation for the detection of multiple color targets, such as the SPS microchip. In addition, the preferred parallel imaging spectrometry apparatus does not contain expensive optics, has no moving parts (except for the translation stage) and provides for highly parallel, high speed signal detection.

B. The Microarray Format

Miniaturized oligonucleotide arrays for mutation detection present a strategy for overcoming the problems associated with gel-based methods (DeRisi et al., *Nature Genetics* 14:457–460 (1996), herein incorporated by reference in its entirety; Hacia et al., *Nature Genetics* 14:441–447 (1996), herein incorporated by reference in its entirety; Head et al., *Nucleic Acids Res.* 25:5065–5071 (1997)). The present invention offers significant advantages over gel-based sequencing methods in several areas, including sample processing simplicity, through-put and reagent cost. These advantages are realized because microarray technology allows for highly parallel analysis of samples with minimal reagent usage and purification steps. For example, a 10 μl multiplexed PCR reaction can be hybridized simultaneously to hundreds or thousands of oligonucleotides in an array only a few millimeters in diameter. In this way, processing is performed on a "macro" scale, using standard pipettes, with the information being extracted on a "micro" scale, using fluorescent imaging.

Microarray technology is presently being used to study gene expression (Schena et al., *Proc. Natl. Acad. Sci.* (U.S.A.) 93: 10614–10619 (1996); Schena, *Bioessays* 18: 427–431 (1996), both of which are herein incorporated by reference in their entirety), determine gene function (Shoemaker et al., *Nature Genetics* 14:450–456 (1996), herein incorporated by reference in its entirety), analyze polymorphisms (Nikiforov et al., *Nucleic Acids Res.* 22:4167–4175 (1994), herein incorporated by reference in its entirety) and fingerprint DNA (Salazar et al., *Nucleic Acids Res.* 24:5056–5057 (1996), herein incorporated by reference in its entirety).

1. Array Patterning and Manufacture

The following methods are suitable for immobilizing the sequencing reagent of the present invention. Although covalent attachment methods are the preferred methods of immobilizing the sequencing reagents of the present invention, it is to be understood that the conventional non-covalent immobilization methods are also suitable for use in the present invention. Under an alternative embodiment, the sequencing reagents are in solution.

Holmstrom et al., for example, exploit the affinity of biotin for avidin and strepavidin, and immobilize biotinylated nucleic acid molecules to avidin/strepavidin coated supports (Holmstrom et al., *Anal. Biochem.* 209:278–283 (1993), herein incorporated by reference in its entirety). Another method requires the pre-coating of the polystyrene or glass solid phases with poly-L-Lys or poly L-Lys, Phe, followed by the covalent attachment of either amino- or sulfhydryl-modified oligonucleotides using bi-functional crosslinking reagents. Both methods require the use of modified oligonucleotides as well as a pretreatment of the solid phase (Running et al., *Bio/Techniques* 8:276–277 (1990); Newton et al. *Nucleic Acids Res.* 21:1155–1162 (1993), both of which are herein incorporated by reference in their entirety).

Kawai et al. describe an alternative method in which short oligonucleotide probes were ligated together to form multimers and these were ligated into a phagemid vector (Kawai et al., *Anal. Biochem.* 209:63–69 (1993), herein incorporated by reference in its entirety). The oligonucleotides were immobilized onto polystyrene plates and fixed by UV irradiation at 254 nm. A method for the direct covalent attachment of short, 5'-phosphorylated primers to chemically modified polystyrene plates ("Covalink" plates, Nunc) has also been proposed by Rasmussen et al., *Anal. Biochem.* 198:138–142 (1991), herein incorporated by reference in its entirety. The covalent bond between the modified oligonucleotide and the solid phase surface is created by a condensation reaction with a water-soluble carbodiimide. The Rasmussen et al. method concerns a predominantly 5'-attachment of the oligonucleotides via their 5'-phosphates; however, it requires the use of specially prepared, expensive plates.

Maskos et al. describe a method to synthesize oligonucleotides directly onto a glass support (Maskos et al., *Nucl. Acids Res.* 20:1679–1684 (1992), herein incorporated by reference). According to this method, a flexible linker with a primary hydroxyl group is bound to the solid support via a glycidoxypropyl silane, wherein the primary hydroxyl group serves as the starting point for the oligonucleotide synthesis. The disadvantages of this method are that the reaction is not reversible and the oligonucleotides leak from the solid surface during manipulation.

Covalent disulfide bonds have been previously used to immobilize both proteins and oligonucleotides. Carlsson et al. disclose a method for the reversible immobilization of thiolated proteins and peptides to an agarose bead by means of a disulfide bond (Carlsson et al., *Biotech. Applied Biochem.* 14:114–120 (1991), herein incorporated by reference in its entirety). In that method, the disulfide bond is formed between a thiol containing protein and a thiol-derivatized agarose bead. The reference also discloses that the disulfide bond is reversible in the presence of an excess of dithiothreitol. Chu et al. (*Nucleic Acids Res.* 16: 3671–3691 (1988), herein incorporated by reference in its entirety) disclose a method for coupling oligonucleotides to nucleic acids or proteins via cleaveable disulfide bonds. Prior to the coupling reaction, the oligonucleotides are modified by adding a cystamine group to the 5' phosphate by means of a phosphoramadite bond. Sliwkowski et al. discloses a method of covalent chromatography wherein proteins are immobilized to cysteinylsuccinimidoproyl glass beads through reversible disulfide bond interaction (Sliwkowski et al., *Biochem. J.* 209: 731–739 (1983), herein incorporated by reference in its entirety).

Fahy et al. describe the synthesis of 5'-bromacetyl and 5'-thiol oligonucleotide derivatives and the covalent immobilization of these oligonucleotide derivatives via thioester bonds to sulfhydryl- and bromacetyl-modified polyacrylamide supports. The disadvantage of this method is that the covalent bond is not reversible (Fahy et al., *Nucleic Acids Res.* 21: 1819–1826 (1993), herein incorporated by reference in its entirety).

Anderson et al. describe a novel method for immobilizing nucleic acid molecules to a solid-phase by means of a reversible, covalent disulfide bond (PCT/US98/04114, herein incorporated by reference in its entirety). In that method, a disulfide bond is formed between a thiol or disulfide containing nucleic acid molecule and a mercaptosilane coated solid surface. Shi et al. (U.S. patent application Ser. No. 08/870,010, herein incorporated by reference in its entirety), describe a method for immobilizing nucleic acid molecules to a solid phase by means of a covalent ether or thioether linkage. These simple, two-step methods have the specificity and efficiency needed to prepare DNA arrays suitable for use in the present invention.

Although all of the above described methods can be used to immobilize the sequencing reagent of the present invention to the solid support, the preferred embodiments for immobilizing a sequencing reagent to a solid support are disclosed by Anderson et al. and Shi et al. An additional preferred embodiment for immobilizing the sequencing reagent of the present invention is to immobilize biotinylated nucleic acid molecules to avidin/strepavidin coated supports as disclosed by Holmstrom et al., *Anal. Biochem.* 209:278–283 (1993), herein incorporated by reference in its entirety.

Although the microchip may be made of a variety of glass or plastic solid supports, glass is the preferred solid support. Preferably, the solid support is fashioned as a microscope slide, coverslip, a capillary tube, a glass bead or a channel. The solid support can also be a glass plate, a quartz wafer, a nylon or nitrocellulose membrane or a silicon wafer. However, the support can further be fashioned as a bead, dipstick, test tube, pin, membrane, channel, capillary tube, column, or as an array of pins or glass fibers. Although glass is the preferred solid support, the solid support can also be plastic, preferably in the form of a 96-well plate or 384-well plate. Preferably, the plastic support is a form of polystyrene plastic.

Currently, 96-well polystyrene plates are widely used in solid-phase immunoassays, and several PCR product detection methods that use plates as a solid support have been described. The most specific of these methods require the immobilization of a suitable oligonucleotide probe into the microtiter wells followed by the capture of the PCR product by hybridization and colorimetric detection of a suitable hapten. However, solution based methods can also be employed.

The sequencing reagents of the present invention are intended to be made into an array. As used herein, the phrase "sequencing reagent" is intended to refer to a reagent which is capable of being extended in a polymerase-mediated, template-dependent fashion. Accordingly, the phrase is intended to encompass DNA, RNA and PNA sequences or combinations thereof. The sequencing reagents of the present invention can be either synthetically or naturally made. As used herein, a natural sequencing reagent includes, but is not limited to, such reagents as a gene or fragment thereof, a cDNA molecule or fragment thereof, and an EST molecule or fragment thereof. As used herein, an array is an orderly arrangement of sequencing reagents, as in a matrix of rows and columns or spatially addressable or separable arrangement such as with coated beads. Preferably, the array is an array of nested sequencing reagents. As used herein, a nested array is an array of reagents whose sequence specific hybridization regions sequentially overlap in sequence. By using an array of nested sequencing reagents, it is possible to determine the sequence of the target nucleic acid.

With an automated delivery system, such as a Hamilton robot (e.g., Hamilton 2200 pipeting robot (Hamilton, Inc., Reno, Nev.)) or ink-jet printing method, it is possible to form a complex array of oligonucleotide probes on a solid support, in particular an epoxysilane, mercaptosilane or disulfidesilane coated solid support. Such methods can deliver nano to pico-liter size droplets with sub-millimeter spacing. Because the aqueous beads are well defined on such a hydrophobic surface, it is possible to create an array with a high density of oligonucleotide probes. Thus, it is possible to create arrays having greater than about 10,000 probe droplets/cm$^2$. Such arrays can be assembled through the use of a robotic liquid dispenser (such as an ink-jet printing device controlled by a piezoelectric droplet generator) such that each nucleic acid molecule occupies a spot of more than about 10 microns, preferably more than 25 microns in diameter and each nucleic acid spot is spaced no closer, center to center, than the average spot diameter. Methods and apparatuses for dispensing small amount of fluids using such ink-jet printing techniques and piezoelectric ink-jet depositions have been previously described by Wallace et al. (U.S. Pat. No. 4,812,856), Hayes et al. (U.S. Pat. No. 5,053,100), both of which are herein incorporated by reference in their entirety.

Under one embodiment, the array can be constructed using the method of Fodor et al. (U.S. Pat. No. 5,445,934, herein incorporated by reference in its entirety). Fodor et al. describe a method for constructing an array onto a solid surface wherein the surface is covered with a photo-removable group. Selected regions of the substrate surface are exposed to light to as to activate the selected regions. A monomer, which also contains a photo-removable group, is provided to the substrate surface to bind to the selected area. The process is repeated to create an array.

Under another preferred embodiment, the array can be created by means of a "gene pen". A "gene pen", as used herein, refers to a mechanical apparatus comprising a reservoir for a reagent solution connected to a printing tip. The printing tip further comprises a means for mechanically controlling the solution flow. Under one embodiment, a multiplicity of "gene pens" or printing tips may be tightly clustered together into an array, with each tip connected to a separate reagent reservoir. Under another embodiment, discrete "gene pens" may be contained in an indexing turntable and printed individually. Typically, the solid surface is pretreated to enable covalent or non-covalent attachment of the reagents to the solid surface. Preferably, the printing tip is a porous pad.

Alternatively, the array can be created with a manual delivery system, such as a pipetman. Because these arrays are created with a manual delivery system, these arrays will not be as complex as those created with an automated delivery system. Arrays created with a manual delivery system will typically be spaced, center to center, >2 mm apart. Preferably, arrays created with a manual delivery system will be created in a 96-well or 384-well plate. Therefore, depending on the delivery system employed, it is possible to create arrays spaced, center to center, with >2 mm spacing, 0.5–2 mm spacing, 50–500 µm spacing or >50 µm spacing.

II. Hyperspectral Imaging Methodology

The present invention provides a method for hyperspectral imaging chain-terminating nucleotide analogs used in nucleic acid sequencing. Preferably, the chain-terminating nucleotide analogs of the present invention are dideoxynucleotide analogs. Under a preferred embodiment, the chain-terminating nucleotide analogs of the present invention are detectably labeled. More preferably, the detectably labeled chain-terminating nucleotides are fluorescently labeled. Preferably, the present invention employs four differentially labeled chain-terminating nucleotide analogs. Under one embodiment, the fluorescently labeled chain-terminating nucleotide analogs are the ABI terminators Fam-ddCTP, Joe-ddATP, Tamra-ddGTP and Rox-ddTTP (Synthetic Genetics, San Diego, Calif.). Additional florescent molecules suitable for use in the present invention include, but are not limited to, fluorescein, rhodamine, texas red, HEX, TET, Cy3, Cy3.5, Cy5, Cy5.5, IRD40, IRD41 and BODIPY. Preferably, the selected fluorescent dye has an emission region selected from about 530 nm to about 630 nm.

A. Solid-Phase Sequencing (SPS) Methodology

DNA array sequence analysis methods have, for the most part, depended on hybridization to discriminate and detect non-wild type bases in the target sequence. The hybridization-based approach is inherently sensitive to small changes in hybridization conditions and can require sophisticated analysis of high numbers of oligonucleotide probes (twenty or more per base of the target sequence), under two or more sets of hybridization conditions, in order to accurately determine the nature and location of mutations in the targeted region (Hacia et al., *Nature Genetics* 14:441–447 (1996)).

Preferably, solid-phase primer extension biochemistry, Genetic Bit Analysis, or GBA™ (Nikiforov et al., *Nucleic Acids Res.* 22:4167–4175 (1994)), is employed in the present invention for nucleotide-by-nucleotide sequence analysis. This nucleotide-by-nucleotide sequence analysis strategy is achieved through the use of a template dependent polymerase-mediated extension of the hybridizing interrogation primer with labeled ddNTPs. The addition of a polymerase mediated primer extension to solid-phase analysis results in a significant increase in test accuracy and differential sensitivity over hybridization-based approaches.

Solid-phase sequencing (SPS) by GBA has been reported to provide detailed and accurate sequence analysis with a minimal number of probes per base in the target sequence (Head et al., *Nucleic Acids Res.* 25:5065–5071 (1997), herein incorporated by reference in its entirety). The SPS method increases the flexibility and utility of solid-phase primer array mutation analysis by exploiting the advantages of primer extension biochemistry over differential hybridization for DNA sequence analysis. This results in a dramatic reduction in the number of probes required per target base, as compared to standard hybridization-based methods for detection and positioning of mutations (Hacia et al., *Nature Genetics* 14:441–447 (1996)).

1. Four-Dye Label Fluorescent SPS Strategy

Preferably, the present invention employs fluorescent detection strategies. Fluorescent detection strategies have been widely accepted as simpler and safer alternatives to the traditional radioisotope and indirect ELISA methods for detection of biomolecules. However, it is understood that the present invention can also employ traditional radioisotope detection strategies as well as indirect ELISA methods and other standard detection methodologies.

Fluorescent-based strategies have been reported to be viable detection methods for nucleic acid sequencing (Smith et al., *Nature* 321:674–679 (1986); Prober et al., *Science* 238:336–341 (1987), both of which are herein incorporated by reference in their entirety). Fluorescent detection methods provide advantages over radioisotope and ELISA methods in the areas of sensitivity, safety, and compatibility with automation and operational simplicity. Most importantly, they allow multiple analyses to be resolved in the same sample by spectrally resolving different fluorescent labels.

Figure 3:
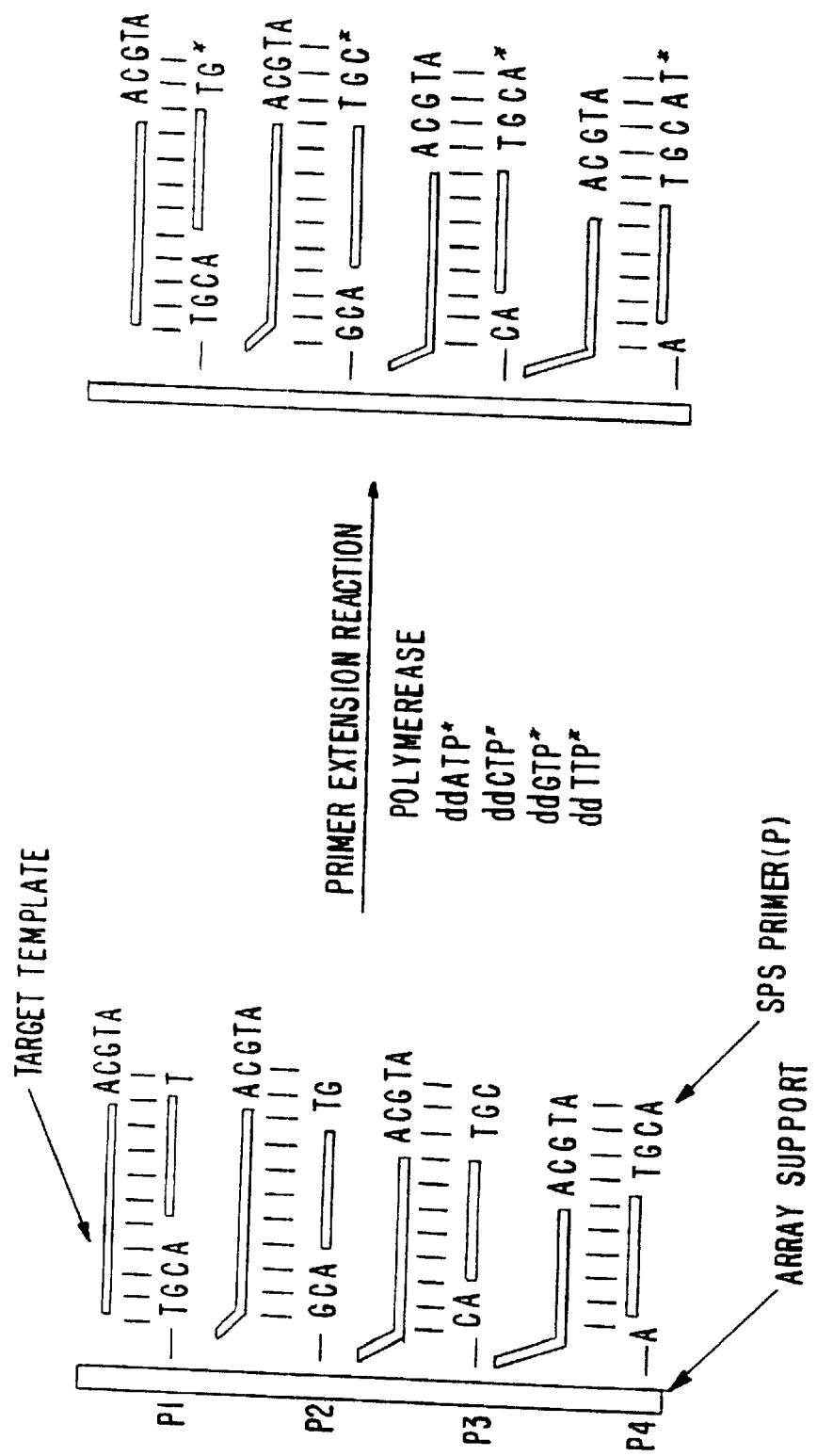
FIG. 3 provides an illustration of the SPS biochemistry of the present invention.

Under a preferred embodiment of the present invention, the SPS array strategy is further realized by the use of four-color direct fluorescent detection technology. By using a mixture of four different dye-labeled ddNTPs in a single extension reaction, four independent extension reactions can be performed simultaneously on one array, instead of on four separate arrays with four, single dye terminator mixes (this is analogous to labeled primer sequencing requiring four lanes/sample vs. dye terminator sequencing, requiring only a single lane per sample). Detection of the extension products can then be identified by spectrally resolving the different fluorescent labels. The four-dye terminator SPS biochemistry is illustrated in FIG. 3.

The four-color detection SPS strategy of the present invention further simplifies sample processing procedures, minimizes liquid handling requirements, reduces reagent consumption and increases the information density obtained per array per reaction. Moreover, the use of a single microarray for the analysis of extension reactions of all four bases avoids complications inherent in comparing results from independent hybridization and extension reactions on different spots and/or arrays, thus increasing the robustness and accuracy of base recognition and calling. Furthermore, direct detection of fluorescent signals from SPS arrays can be accomplished through the use of a non-confocal strategy.

B. Dye/base Misclassification in Fluorescent Detection

In fluorescent-based sequencing applications, base calling decisions can be made by comparing the detected spectral patterns (the fraction of the emission detected through different filters) of an unknown base/dye with the normalized spectral patterns of the known individual dye-labeled ddNTPs. The spectral misclassification, or the probability of miscalling, can be estimated by using Cramers' inequality routine that leads to the classification formula below (Kolner, *Applied Optics* 32:806–820 (1993), herein incorporated by reference in its entirety):

$$I_d = \Sigma_f (n_d^f) \times Ln[(n_d^f/N_d) \times (1/p^f_d)],$$

where
d—dyes (A, C, G or T)
f number of emission filters
$n_d^f$ signal of d dye through f filter
$N_d = \Sigma_f n_d^f$ summary signal of d dye
$p^f_d$ pattern, normalized signal of individual d dye through f filter Using this classification formula, the measurement of an unknown dye/base can be compared to the known spectral patterns to find the best match. The confidence in the accuracy of base/dye calling is highest when $I_d$, which represents the discrepancy between the measurement and pattern, is minimized. The presence of a noise component in fluorescent signals ($n_f$) will result in miscalling. Preferably, a computer program (e.g., MathCad software (MathSoft, Inc., Cambridge, Mass.)) that calculates $I_d$ statistics for varied fluorescent signal-to-noise ratio (SNR), is used to generate detection patterns for any dye-filter (d-f) combination. Preferably, the computer program would allow for the quantitative evaluation of the miscalling rate and spectral selectivity for any SNR.

Under an alternative embodiment, data-adaptive algorithms for base calling can be used in the present invention (Stoughton et al., *Electrophoresis* 18:1–5 (1997), herein incorporated by reference in its entirety). Under another embodiment, the base-calling program Sax can be used in the present invention (Kheterpal et al., *Electrophoresis* 17:1852–1859 (1996)).

The presence of biochemical noise caused by misincorporation or false priming can interfere with the base calling. The most common source of noise in GBA reactions, template independent noise (TIN), is caused by self-priming of GBA primers. TIN can be reduced by replacement of key bases (bases that function as a template in self-priming reactions) in the GBA primers with basic linkers. Using this method, it is possible to minimize TIN by >99%. Another source of noise in GBA is template-dependent noise (TDN), caused by false priming of the template. These sources of noise could complicate the multi-color dye/base identification. TDN can be minimized by increasing the stringency of the hybridization and extension reactions. Variable extension efficiency and specificity from different dye terminators may also been seen. Optimization of the extension reaction and adjustment of the relative concentrations of the dye terminators may minimize the differences.

C. Selection of Spectral Resolution

The selection and limitation of spectral resolution is determined by the spectral characteristics of the selected dyes. The ratio of the central wavelength to the width of the emission/absorption spectra of the four ABI dyes is approximately 15. Therefore, a relatively low spectral resolution can be used for the complete spectrum detection of the four ABI dyes. It is understood that different spectral decomposition optics (diffractive and dispersion) can be used to accomplish optimal spectral discrimination. Based on the separation of ABI dyes' spectra, which is approximately 25 nm, the preferred spectral resolutions range from 1 to 5 nm.

D. Imaging Capacity

After the selection of spectral resolution, it is preferable to maximize the information capacity of array spectral imaging. For a spectral imaging region of 530–630 nm with 2 nm resolution, 50 spectral pixels are generally required. This can limit the number of DNA chip sites along the dispersion direction (approximately 20) in a standard, cooled CCD with 1000×1000 pixels. The limit of spectral imaging capacity has been estimated to be approximately $10^4$ sites per 1 $cm^2$ (approximately $10^3$ in one axis×20 in another axis) with 1:1 amplification of imaging optics if the size of each spot on the microarray is larger than the pixel size. Therefore, array spectral analysis can be complicated by geometrical and spectral image overlapping of the sites.

Use of a single, point-like emission source is theoretically optimal for spectral detection. Because the microarray sites of the present invention are detected by a focused line and not by a point light source, the spectral images of an array's sites may partially overlap. When spectral images overlap, spectral information can be lost.

Under a preferred embodiment, a deconvolution technique for extraction of spectral information from overlapping images can be used. This technique optimumizes the spectral imaging capacity for any spot size on an array. Deconvolution in hyperspectral imaging is a software program which corrects the detected spectra through mathematical separation of the spectra of the individual microarray spots. Thus, deconvolution helps to eliminate overlapping effects induced by microchip geometry and spectrometer optics (instrument apparatus function). In hyperspectral parallel detection, deconvolution can be used if spectral and/or spatial resolution of the imaging spectrometer results in a loss of the emission spectrum information of each site in an array.

E. Spectral Discrimination of Dye-Labels

Under a preferred embodiment, spectral recognition patterns for all four dye-labels from emission spectra of solid-phase bound dye-labeled oligomers are developed. The present invention can employ anywhere from 10 to 150 spectral channels. Preferably, the present apparatus employs from 20 to 100 spectral channels. More preferably, the present sequencing apparatus employs from about 20 to about 50 spectral channels and most preferably the patterns include fifty spectral channels. The number of spectral channels is determined by the spectral detection range and selected spectral resolution. Under a preferred embodiment, the spectral detection range is 530–630 nm and the selected spectral resolution is 2 nm. However, it is to be understood that the spectral detection range can be broader than 530–630 nm. The only limit on the spectral detection range is the availability of suitable fluorescent dyes. It is further to be understood that although the preferred spectral resolution is 2 nm, spectral resolutions range from 1 to 5 nm are suitable for use in the present invention.

These developed patterns can be applied to dye/base recognition on microarrays. A statistical analysis for the miscalling rate of all four dye-labels using fifty spectral channels is preferably performed. The results of this analysis can be applied to the optimization of spectral selectivity of the instrumentation.

F. Entire Array Hyperspectral Imaging

Within a DNA microchip, individual reaction sites are small-size fluorescence emitters located separately in an array plane. One may consider each of these emitters as a part of the illuminated entrance slit of the spectrometer or a full collection of emitters (emitted fluorescence array) as a combination of these parts for many different spectrometers. Based on this concept, hyperspectral array imaging can be accomplished by the implementation of dispersion optics in collimated array emission and detection of spectrally dispersed fluorescence by a 2-D imaging detector (CCD). Although this approach can limit the detectable array density by the double use of dispersion, it allows for simultaneous imaging, in real-time, of the entire microarray with a density of about $10^3$ sites/$cm^2$. Therefore, it is highly compatible with high-speed and high throughput detection of microarrays. Diffractive (grating) and disperse (prism) optics can be used in the present invention.

In order to increase the spectral selectivity, the present invention can also include the introduction of additional excitation and/or emission channels and the use of a microchip support with lower fluorescent background.

Having now generally described the invention, the same will be more readily understood through reference to the following examples which are provided by way of illustration, and are not intended to be limiting of the present invention, unless specified.

EXAMPLE 1

Direct Fluorescent Image of a GBA Array

Target template is hybridized onto an array, with GBA primer extension reactions being performed with fluorescein-labeled dideoxy nucleotides using standard GBA protocol (Nikiforov et al., *Nucleic Acids Res.* 22:4167–4175 (1994), herein incorporated by reference in its entirety). The GBA signals are detected by exciting the extended oligonucleotide array with a CW Ar laser (excitation wavelength 488 nm, power density 10 mW/cm$^2$) and capturing the fluorescent emissions using a cooled CCD camera (SPECIM-1A, First Magnitude Corp.) with an integration of one second and 8×8 binding. Color glass OG 530 and a bandpass interference filter (535±10 nm) are used to select the detection region.

Figure 4:
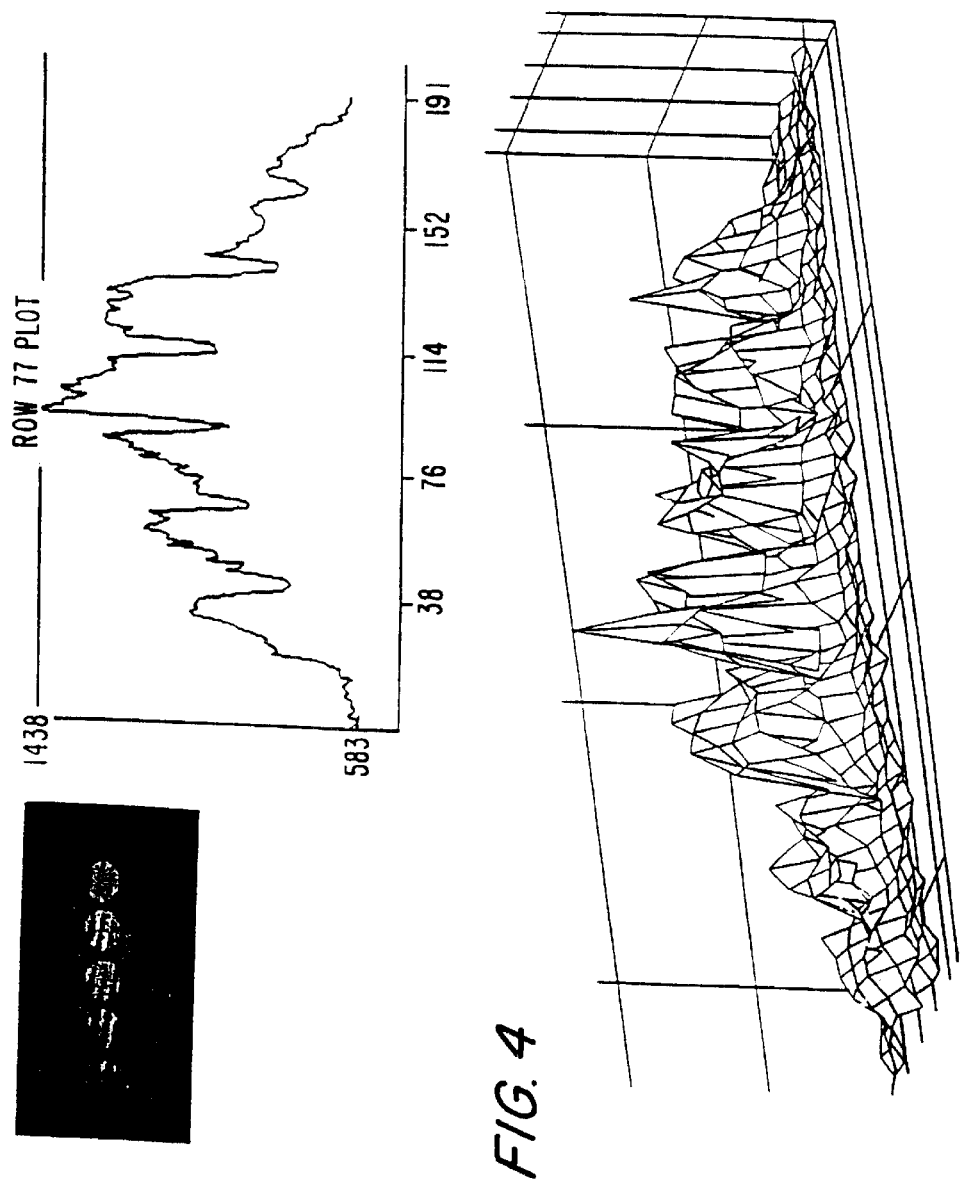
FIG. 4 provides a direct fluorescent image of a GBA array.

The direct fluorescent image of a GBA array via a CCD camera is depicted in FIG. 4. Upper-left panel in FIG. 4 shows CCD false-color image; upper-right panel shows the CCD row reading; and the bottom panel shows the 3D contour image. Horizontal lines in the false-color array image are the interference patterns generated by interaction of excitation beam and the reflected beam (from the bottom of the slide). Spatial Fourier-transform filtering of the modulated image may be used for the elimination of background emissions (Bogdanov et al., In: *Ultrasensitive Biochemical Diagnostics II*, Cohen and Soper, eds. *Proceedings of SPIE* 2985:129–137 (1997), herein incorporated by reference in its entirety). The glass slide background forms a smooth curve underlying a composite (GBA+background) emission (upper-right panel). The background contributes approximately 30% in detected microchip fluorescence. The signal to noise ratio (SNR) of direct fluorescent GBA imaging detection is approximately 10:1.

Fluorescent Imaging of High-density Arrays

An entire image of a microchip array (1×1 cm$^2$ area) is captured by using a standard cooled CCD (1000×1000 pixel format, 10$\mu$ pixel size) with 1×1 amplification optics. In this case, the spatial resolution of the detection system is equal to the CCD pixel size (=10$\mu$). This spatial resolution is sufficient for the detection of a GBA array with a density of greater than 10,000 spots/cm$^2$. Resolution and sensitivity of CCD fluorescent imaging for a DNA microchip is illustrated by FIG. 5 which demonstrate that the CCD detector is capable of detecting 10$^{-18}$ M of fluorescently labeled oligo molecules with a resolution of at least 70$\mu$.

Figure 5:
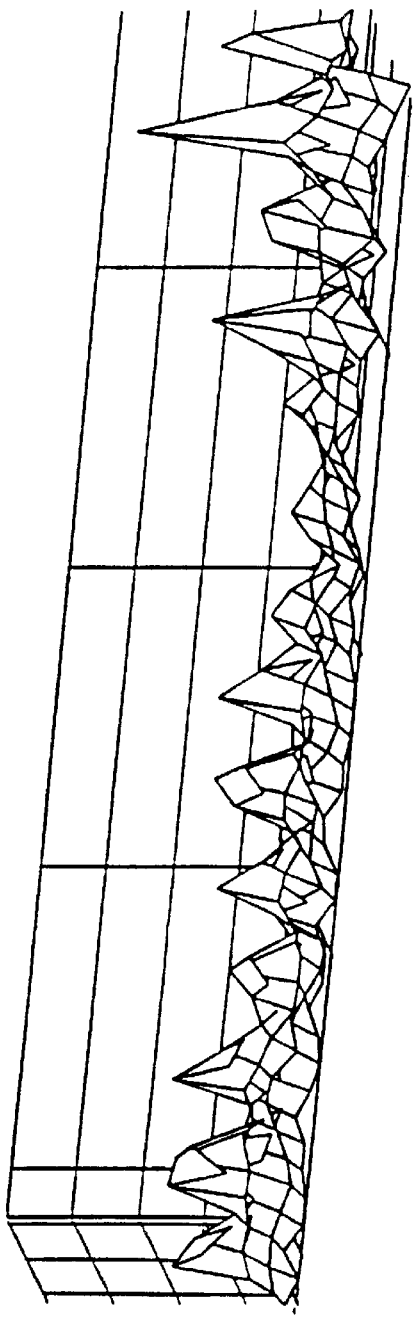
FIG. 5 illustrates the fluorescent image of a GBA array manufactured on a microscope glass slide.

The CCD fluorescent image of a fluorescent oligonucleotide array manufactured by inkjet printing method is provided in FIG. 5. Fluorescent-labeled oligonucleotides are dispensed by ink-jet printing and immobilized on a microscope slide. The fluorescent-labeled oligonucleotides are attached to the microscope slide using the attachment chemistry of Anderson et al. (Ser. No. 08/812,010, filed on Mar. 5, 1997). Alternatively, the fluorescent-labeled oligonucleotides can be attached to the microscope slide using the attachment chemistry of Shi et al. (U.S. patent application Ser. No. 08/870,010). The spot spacing is 125$\mu$ center to center, the droplet volume is 0.25 nL and the spot diameter is 70$\mu$. The deposition of 0.25 nL oligos solution should result in the immobilization of approximately 10$^{-18}$ M oligonucleotide molecules. The fluorescent image of the ink-jet printed array is captured by a SPECIM-1A CCD with 2×2 binning and an integration time of 5 seconds. Excitation is by a CW Ar laser with a power density of approximately 5 mW/cm$^2$.

The MathCad program (MathSoft, Inc., Cambridge, Mass.) is used to calculate the miscalling rate for an ABI sequencer. Analysis of the spectral characteristics of the four ABI dye-labels and the four bandpass filters (each with 10 nm spectral width) used by the ABI sequencer (Kolner, *Applied Optics* 32:806–820 (1993)) results in a detection pattern shown in Table 1. Columns 1–4 of Table 1 show a normalized detection pattern (the product of filter transmission and dye emission spectra) for each of the four ABI dye-base/filter combinations.

TABLE 1

| Dye/Filter | 1 | 2 | 3 | 4 |
|---|---|---|---|---|
| Fam-C | 0.39 | 0.31 | 0.21 | 0.09 |
| Joe-A | 0.25 | 0.4 | 0.25 | 0.1 |
| Tamra-G | 0.04 | 0.16 | 0.5 | 0.3 |
| Rox-T | 0.01 | 0.03 | 0.14 | 0.8 |

Computer-generated Gauss distributed random noise is introduced to the $n_d^f$ value of the classification formula to simulate the presence of a noise component in the detected signals. The statistical calculation performed on the ABI sequencer miscalling rate is based on 10,000 tests and the results are presented in Table 2. The data in Table 2 shows that the miscalling rates (last column) increase rapidly when the noise increases. Also, there is a significant difference in the miscalling rate for different dye-bases. This difference is the result of variations in dye spectral cross-talk and spectral selectivity of ABI filters for individual dye-labels. The first column of Table 2 shows SNR values; the last column shows the number of mis-calling for a given SNR. The letters T, G, A and C in the first row indicate the bases (see Table 1, dye-base combination) that contribute to the fluorescence signal. The letters in the second row indicate the bases that do not contribute to fluroescence signals. Noise induces false classification of these bases and the frequency of the false classification determines the miscalling rate.

TABLE 2

| SNR | T | | | G | | A | | C | | | | Sum. |
| | G | A | C | T | A | C | C | G | T | A | G | T | Mis-Class |
|---|---|---|---|---|---|---|---|---|---|---|---|---|---|
| 100:4 | 0 | 0 | 0 | 0 | 0 | 0 | 0 | 0 | 0 | 0 | 0 | 0 | 0 |
| 100:8 | 86 | 0 | 0 | 0 | 0 | 0 | 5 | 0 | 0 | 11 | 0 | 0 | 102 |
| 100:12 | 1080 | 60 | 18 | 0 | 10 | 0 | 66 | 0 | 0 | 160 | 0 | 0 | 1394 |
| 100:16 | 5000 | 600 | 185 | 0 | 200 | 11 | 300 | 0 | 0 | 780 | 0 | 0 | 7076 |

Figure 6:
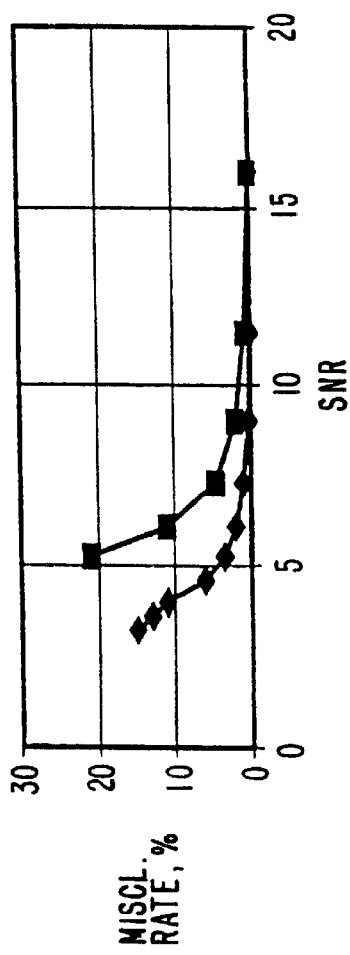
FIG. 6 illustrates the base misclassification rate versus Signal to Noise Ration (SNR) at different spectral selectivity.

FIG. 6 illustrates the dependence of the miscalling rate on spectral selectivity of the detection system. This figure shows the results of statistical calculations made for Joe-A and Fam-C (ABI dye-base) using two- and four- ABI filter detection and with variable noise contribution. Higher spectral selectivity (four-filter detection) results in significantly better classification than two-filter detection with the same SNR. Analysis of the above shows that complete spectrum detection provides better analytical selectivity than does detection where the number of bandpass filters is equal to the number of dye-bases. Implementation of a detection system with high spectral selectivity is used in cases of low SNR (i.e., detection of weak fluorescence). In DNA chip technology, the fluorescence signal can be limited by the number of dye-labeled ddNTP molecules available at the oligonucleotide probe site on a confined, high-density array. Based on this consideration, it is preferred that the hyperspectral detection maximizes the analytical power of the spectral instrumentation chosen as the main of the fluorescent instrumentation used in SPS microarray mutation scanning with four dye-labeled terminators.

Microarray Parallel Fluorescent Spectrometry

The complete spectral detection of a DNA microchip is performed with a commerically available Imaging Spectrometer (Cromex, Inc., Model 250 1S). A block diagram of the hyperspectral imaging apparatus is provided in FIG. 1. The laser beam is focused by cylindrical lens into a thin line on the microchip surface and a collection lens projects the fluorescence of the illuminated microchip row along the specrometer's entrance slit. Multiple spectra of microchip sites in the laser illuminated area (parallel fluorescent spectrometry) are detected on the spectrometer's focal plane by a cooled CCD (SPECIM-1A). The microchip is moved across the excitation beam by a precise translation stage (Acturator 850B, Motion controller PMC 100; Newport Corp.), allowing complete spectral detection of the complete microchip area.

Figure 7:
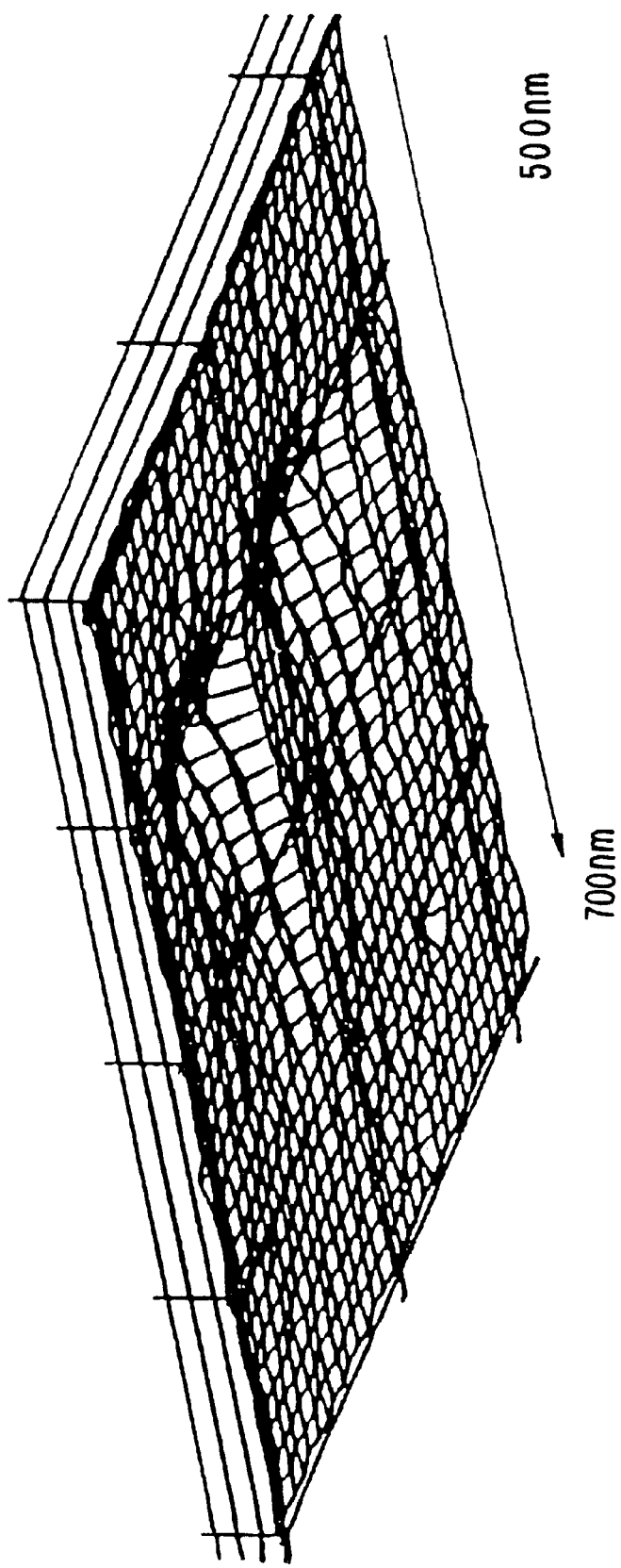
FIG. 7 provides the CCD fluorescent image of a fluorescent oligonucleotide array manufactured on a glass slide.

FIG. 7 provides the parallel spectral detection of fluorescent labeled oligos immobilized onto a microscope slide in two groups of four spots with using the conditions described above. The excitation source used in this experiment is an Ar laser (488 nm). The complete spectral image is captured through a 535/25 nm interference filter by a SPECIMA-1A CCD camera with an integration time of five seconds and 2×2 binning. The array is excited by a CW Ar laser at a power denisty of approximately 5 mW/cm$^2$.

EXAMPLE 2

SPS Scanning of p53 Sequence

Figure 8:
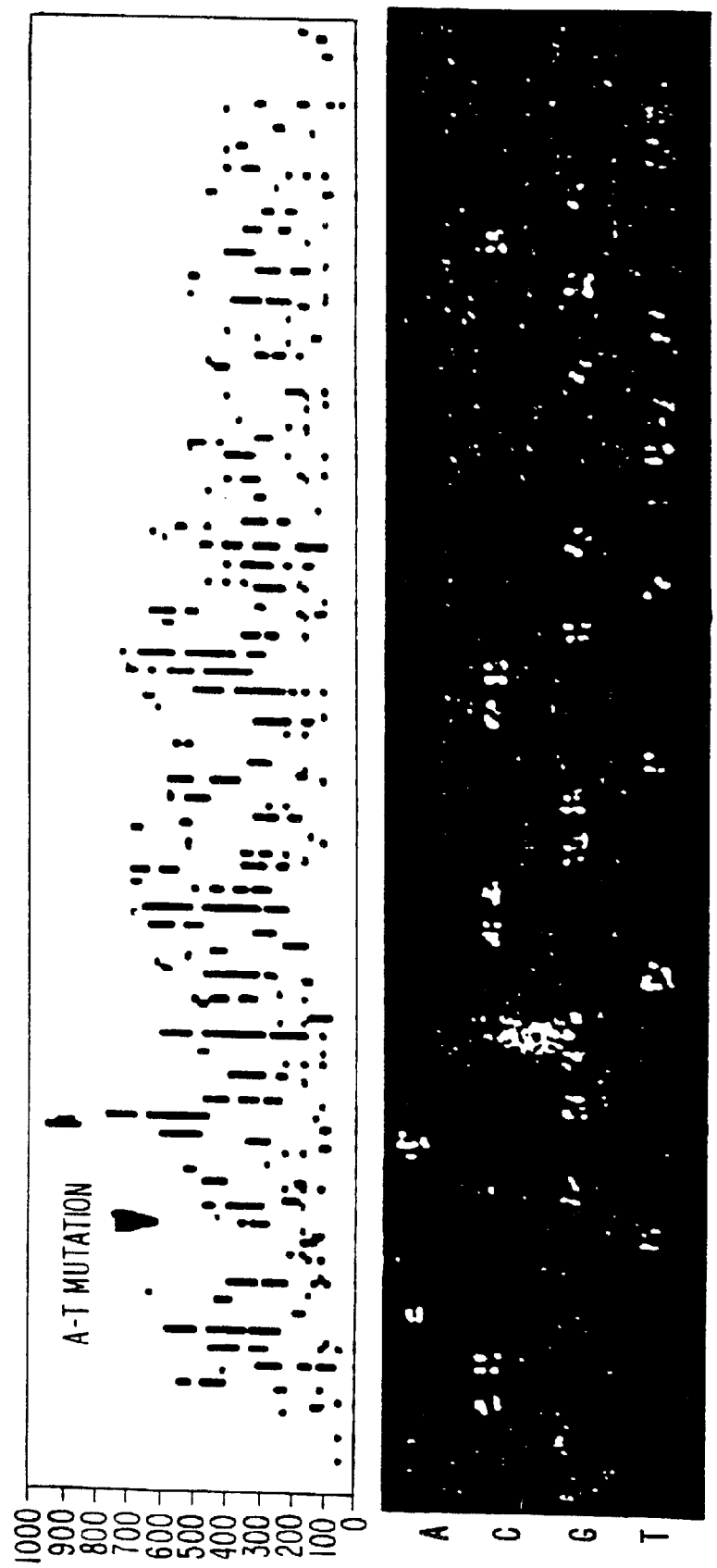
FIG. 8 provides the CCD image and profile for an SPS array scan of a DNA template matching partial sequence of p53 exon 8 gene.

SPS primers for both strands of a 33 base region of exon 8 of the human p53 gene are synthesized and attached to a silanized glass microscope slides. FIG. 8 provides the results of SPS analysis of a synthetic DNA template hybridized to the arrayed primers and extended with an extension mix containing Klenow DNA polymerase (exonuclease free) and a mixture of dye-labeled and unlabeled ddNTPs. Each of the four lanes on the slide is extended with a ddNTP mixture containing a differently labeled base (as indicated in FIG. 3) in combination with three unlabeled bases. Extension signals are detected indirectly with an anti-FITC alkaline phosphatase conjugate and Molecular Probes' ELF substrate. The image is created by 360 nm illumination and a CCD capture of the emission signals. The DNA template contains an A→T transition at the position indicated by the arrow in FIG. 8.

Similar experiments have been performed with PCR generated templates from a wild type and mutant DNA source. The utility of the SPS microarray for detection of missense, insertion and deletion mutations has been demonstrated on clinically relevant samples (Head et al., *Nucleic Acids Res.* 25:5065–5071 (1997)). The results of SPS mutation detection are confirmed by gel-based sequencing.

EXAMPLE 3

Accuracy of Four Dye Label Detection on SPS Microarrays

Array Format

Arrays with densities of 100 primers/cm$^2$ are assembled using a Hamilton 2200 pipeting robot. Drop sizes of 20 to 30 nL with 0.5–1.0 mm spacing are used to create each array. Ink-jet printing methods are employed for higher density arrays (100–500 micron spacing).

SPS Primer, PCR Primers and Synthetic Template Design

The synthetic templates, PCR primers and SPS primers for both strands of a 67 base region of exon 8 of the human p53 gene are designed based upon established protocols. Synthetic templates, PCR primers and SPS primers are ordered from Research Genetics (Huntsville, Ala.).

Attachment of Primers to Glass

Attachment of 5' disulfide modified oligonucleotides (20–25mers with C18 spacer arm) to glass surfaces is performed via an intermediate mercaptosilane layer using a disulfide bond exchange reaction. This attachment is obtained by a two-step treatment process of silane treatment and oligonucleotide binding. Various glass surfaces, including standard microscope glass slides and cover slips (Cel-Line Associates, Inc. Newfield, N.J.), are etched in 25% aqueous ammonium hydroxide, rinsed in Milli-Q water and then in 95% ethanol. They are treated for 30 minutes in 3-mercapto-propyl-trimethoxysilane (MPTS, Aldrich Chemical Company, Inc., Milwaukee, Wis.) in an acidic buffer of aqueous ethanol (95% ethanol, pH 4.5). Slides are cured for at least 24 hours under dry inert gas (Ar or N$_2$). Cured slides are treated with 5'-disulfide modified oligonucleotides at a 2 to 10 μM concentration in pH 9.0 carbonate buffer (500 mM) and incubated overnight at room temperature. A disulfide exchange reaction between the oligonucleotide 5' RS-group [R=DMTO (CH$_2$)$_6$] and the available thiol of the mercaptosilane yields a disulfide bond between the oligonucleotide and the silane layer.

Solid-phase Hybridization and Extension Reaction

Hybridization salts containing 1.5 mM NaCl, 10 mM EDTA, 1 mM cetyltrimethylammonium bromide (CTAB) and template strands are applied to the glass surface on which the primer has been immobilized. The hybridization reaction is performed at room temperature for 10 to 30 minutes, followed by a TNT (10 mM Tris-HCl, pH 7.5; 150 mM NaCl; 0.05% polyethoxysorbitan 20 (TWEEN 20) wash. After hybridization, polymerase extension mix is applied to the surface. The standard extension mix, containing 1.5 μm of four ABI dye-labeled ddNTPs, Klenow polymerase (exonuclease free); 20 mM Tris-HCl, pH 7.5; 10 mM MgCl$_2$; 25 mM NaCl; 10 mM MnCl$_2$, is applied to the SPS arrays for 5–15 minutes, followed by a TNT wash. The template strands are then stripped from the extended GBA primers by washing with 0.1N NaOH, followed by an additional TNT wash. Extension conditions can be optimized if needed. Factors such as temperature, time of the extension reaction, buffers, enzyme concentration and relative concentrations of each dye terminator can be varied in order to optimize SNR, generate uniform signals and provide reproducible results.

Fluorescence Detection on Solid-phase

After extension, SPS signals are immediately detected with the fluorescent imaging method of the present invention. The quantification of the SPS reaction can done using a software program, (e.g., MTI Image) and base/dye calling results are generated.

Testing of PCR Templates by SPS and Detecting with the Developed Four-dye Imager DNA samples from tumor biopsies containing mutations in the targeted region (at least five sites) are collected. PCR primers are designed to amplify a 100 base region covered by the SPS array. Amplification with primer pairs containing several phosphorothioated bases on one of the primers allows for efficient conversion of double stranded PCR to single stranded template by exonuclease digestion (Nikiforov et al., *PCR Methods and Applications* 3:285–291 (1994), herein incorporated by reference in its entirety). The PCR generated templates are analyzed by the imaging method of the present invention using SPS biochemistry in order to characterize mutations.

Testing of PCR Templates by ABI Sequencing

In order to directly compare the results of SPS sequence analysis with gel-based sequencing, each PCR template is sequenced with an ABI automated DNA sequencer using standard dye terminator chemistry. Heterozygous templates are also sequenced, as described above for SPS scanning. Sequencing gels are analyzed and compared to SPS sequence scans with respect to detection and characterization of mutations, overall accuracy of base calling and detection of mutations in heterozygous templates.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth and as follows in the scope of the appended claims.

I claim:

1. A hyperspectral fluorescent imaging apparatus for microarray detection which comprises:
    (a) a light source, wherein the light source is capable of emitting a transmission beam for hyperspectral fluorescent imaging;
    (b) an expansion lens that expands the transmission beam for microarray detection;
    (c) a focusing lens that focuses the expanded transmission beam into a thin focus line for microarray detection;
    (d) a translation stage;
    (e) a collection lens that collects fluorescent light emitted at the thin focus line;
    an imaging spectrometer for hyperspectral fluorescent imaging; and
    (g) a detector.

2. A hyperspectral fluorescent imaging apparatus for microarray detection which comprises:
    (a) a light source, wherein the light source is capable of emitting a transmission beam for hyperspectral fluorescent imaging;
    (b) a first expansion lens and a second expansion lens that expand the transmission beam for microarray detection;
    (c) a focusing lens that focuses the expanded transmission beam into a thin focus line for microarray detection;
    (d) a collection lens that collects fluorescent light emitted at the thin focus line;
    (e) an imaging spectrometer for hyperspectral fluorescent imaging; and
    (f) a detector.

3. A hyperspectral fluorescent imaging apparatus according to claim 1, wherein the detector is a charge coupled device.

4. A hyperspectral fluorescent imaging apparatus according to claim 1, wherein the light source is a laser.

5. A hyperspectral fluorescent imaging apparatus according to claim 4, wherein the laser is a CW Ar laser.

6. A hyperspectral fluorescent imaging apparatus according to claim 1, wherein the apparatus comprises a first expansion lens and a second expansion lens.

7. A hyperspectral fluorescent imaging apparatus according to claim 2, wherein the apparatus further comprises a translation stage.

8. A hyperspectral fluorescent imaging apparatus according to claim 2, wherein the detector is charge coupled device.

9. A hyperspectral fluorescent imaging apparatus according to claim 2, wherein the light source is a laser.

10. A hyperspectral fluorescent imaging apparatus according to claim 9, wherein the laser is a CW Ar laser.

* * * * *